United States Patent [19]
Craft et al.

[11] Patent Number: 5,613,259
[45] Date of Patent: Mar. 25, 1997

[54] HIGH FREQUENCY ELECTRIC TOOTHBRUSH

[75] Inventors: Adam B. Craft, Fort Collins, Colo.; Keith E. Schleiffer, Gahanna; James E. Dvorsky, Hilliard, both of Ohio; Thomas W. Graves, Fort Collins, Colo.; Ronald B. Gray, III, Columbus, Ohio; Nagabhusan Senapati; Matthew S. Zelinski, both of Worthington, Ohio

[73] Assignee: Teledyne Industries, Inc., Fort Collins, Colo.

[21] Appl. No.: 634,667

[22] Filed: Apr. 18, 1996

Related U.S. Application Data

[63] Continuation of Ser. No. 254,309, Jun. 6, 1994, abandoned.

[51] Int. Cl.[6] ................................................. A46B 13/02
[52] U.S. Cl. .................... 15/22.1; 310/50; 310/68 B; 310/79; 318/119; 388/820
[58] Field of Search .................................. 15/22.1, 22.2, 15/22.4, 23; 318/119; 388/820; 366/276, 601; 310/50, 68 R, 68 B, 79

[56] References Cited

U.S. PATENT DOCUMENTS

| | | |
|---|---|---|
| 1,313,490 | 8/1919 | Larson . |
| 1,517,320 | 12/1924 | Stoddart . |
| 1,832,519 | 11/1931 | Wheat et al. . |
| 2,044,863 | 6/1936 | Sticht ........................................ 15/22.1 |
| 2,158,738 | 5/1939 | Baker et al. . |
| 2,206,726 | 7/1940 | Lasater . |
| 2,246,523 | 6/1941 | Kulik . |
| 2,278,365 | 3/1942 | Daniels . |
| 2,282,700 | 5/1942 | Bobbroff . |
| 2,709,227 | 5/1955 | Foley et al. . |
| 2,734,139 | 2/1956 | Murphy . |
| 2,875,458 | 3/1959 | Tsuda . |
| 2,917,758 | 12/1959 | Held et al. ................................ 15/22.1 |
| 2,977,614 | 4/1961 | Demanuele . |
| 3,104,405 | 9/1963 | Perrinjaquet . |
| 3,145,404 | 8/1964 | Fiedler ........................................ 15/23 |
| 3,159,857 | 12/1964 | Rasmussen . |
| 3,183,538 | 5/1965 | Hübner . |
| 3,316,576 | 5/1967 | Urbush . |
| 3,430,279 | 3/1969 | Hintze ........................................ 15/23 |
| 3,466,689 | 9/1969 | Aurelio et al. . |
| 3,535,726 | 10/1970 | Sawyer . |
| 3,538,359 | 11/1970 | Barowski ................................ 15/22.1 |
| 3,642,344 | 2/1972 | Corker . |
| 3,676,218 | 7/1972 | Sawyer . |

(List continued on next page.)

FOREIGN PATENT DOCUMENTS

| | | |
|---|---|---|
| 1171337 | 1/1959 | France ........................................ 15/22.1 |
| 0033753 | 3/1978 | Japan ........................................ 15/22.1 |
| 435553 | 10/1967 | Switzerland . |
| 609238 | 2/1979 | Switzerland . |
| 899618 | 6/1962 | United Kingdom . |
| WO91/19437 | 12/1991 | WIPO . |
| WO92/10146 | 6/1992 | WIPO . |
| WO92/16160 | 10/1992 | WIPO . |
| WO93/15628 | 8/1993 | WIPO . |

Primary Examiner—Mark Spisich
Attorney, Agent, or Firm—Lee R. Osman

[57] ABSTRACT

An electric oscillating tool, having particular but not necessarily exclusive utility as an electric toothbrush, for driving a brush head assembly or end effector with a resonant mechanism at high frequencies. The electric toothbrush includes handle housing, an electromagnetic motor mounted in the housing, and a mechanical oscillator acted upon by the motor. One end of the mechanical oscillator extends outwardly through an opening in the handle housing while the other end is attached to the housing inside the chamber. The end effector/brush head assembly attaches to the extending end of the mechanical oscillator. A power source supplies an alternating current drive signal to the motor, in turn causing the armature and the mechanical oscillator to oscillate and drive the brush head assembly. Control circuitry senses the frequency of oscillation of the mechanical oscillator and controls the frequency of the drive signal to maintain the mechanical oscillator at resonance under the variety of loads imposed during use.

18 Claims, 10 Drawing Sheets

U.S. PATENT DOCUMENTS

| | | |
|---|---|---|
| 3,840,932 | 10/1974 | Balamuth et al. . |
| 3,882,364 | 5/1975 | Wright et al. . |
| 4,177,434 | 12/1979 | Ida . |
| 4,255,693 | 3/1981 | Keidl . |
| 4,271,382 | 6/1981 | Maeda et al. ............................ 38/820 |
| 4,271,384 | 6/1981 | Beiling et al. . |
| 4,275,363 | 6/1981 | Mishiro et al. . |
| 4,331,422 | 5/1982 | Heyman . |
| 4,381,478 | 4/1983 | Saijo et al. . |
| 4,395,665 | 7/1983 | Buchas . |
| 4,429,997 | 2/1984 | Matthews . |
| 4,522,355 | 6/1985 | Moran . |
| 4,562,413 | 12/1985 | Mishiro et al. . |
| 4,564,794 | 1/1986 | Kilen et al. . |
| 4,698,869 | 10/1987 | Mierau et al. . |
| 4,787,847 | 11/1988 | Martin et al. . |
| 4,811,445 | 3/1989 | Lagieski et al. . |
| 4,871,396 | 10/1989 | Tsujita et al. . |
| 4,873,496 | 10/1989 | Ohgihara et al. . |
| 4,880,382 | 11/1989 | Moret et al. . |
| 4,887,052 | 12/1989 | Murakami et al. . |
| 4,991,249 | 2/1991 | Suroff . |
| 5,095,470 | 3/1992 | Oka et al. . |
| 5,138,733 | 8/1992 | Bock . |
| 5,150,492 | 9/1992 | Suroff . |
| 5,180,363 | 1/1993 | Idemoto et al. . |
| 5,189,751 | 3/1993 | Giuliani et al. ........................ 15/22.1 |
| 5,198,732 | 3/1993 | Morimoto . |
| 5,253,382 | 10/1993 | Beny . |
| 5,263,218 | 11/1993 | Giuliani et al. . |
| 5,294,896 | 3/1994 | Kjellander et al. . |
| 5,305,492 | 4/1994 | Giuliani et al. . |
| 5,309,590 | 5/1994 | Giuliani et al. . |
| 5,311,632 | 5/1994 | Center . |
| 5,378,153 | 1/1995 | Giuliani et al. . |
| 5,383,242 | 1/1995 | Bigler et al. . |

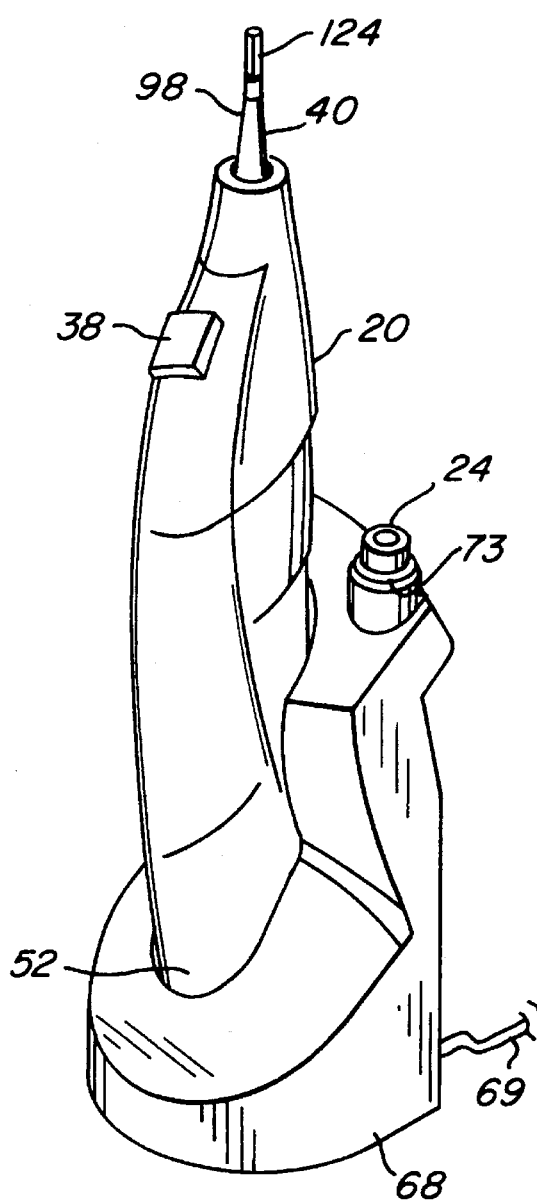
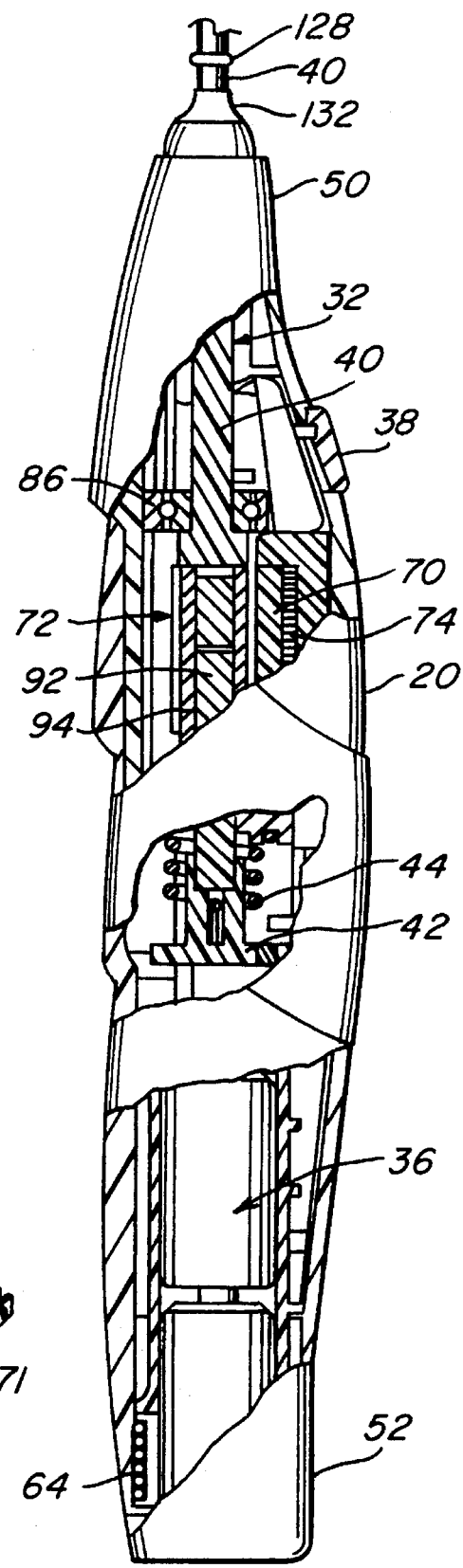
Fig. 7
Fig. 6

HIGH FREQUENCY ELECTRIC TOOTHBRUSH

This is a continuation of application Ser. No. 08/254,309 filed on Jun. 6, 1994, now abandoned.

BACKGROUND OF THE INVENTION

1. Field of the Present Invention

The present invention relates to electric toothbrushes, and more specifically to electromagnetic motor drives that operate at resonant frequency to drive a brush head.

2. Description of the Prior Art

Electric toothbrushes are generally well known. Also well known are the benefits of driving the toothbrush head with a mechanism operating at resonance. At high operating frequencies, driving the toothbrush head by a resonant mechanism maximizes the displacement of the brush head which optimizes the removal of plaque and stains from teeth. The resonant mechanism driving the brush also allows the brush head to move at these higher frequencies with more efficient power usage. Electric toothbrushes provide benefits not obtainable by manual brushing, including more complete and consistent cleaning action.

Numerous electric toothbrushes have been developed that employ spring-mass systems driven by electromagnetic motors operating a resonant mechanism to drive the brush head at resonant frequencies. Typically, the rotor, brush shaft and brush head constitute the mass, while a spring is used to urge the brush shaft to a rest position and assist in obtaining resonant frequency.

U.S. Pat. No. 2,917,758 to Held, et. al., describes an electrically controlled toothbrush having an elongated handle containing an electric motor and a shaft attached to the electric motor. The shaft extends through the handle and terminates in a removable brush head. The shaft is attached to the rotor of the electric motor. When an alternating current is applied to the stator coil, the rotor and shaft are subjected to a reciprocating torque which causes them to rotate in an oscillating manner about the longitudinal axis of the shaft at the frequency of the voltage applied. A spring is connected to the rotor to urge the rotor into a rest position. To maximize the amplitude of the oscillating motion of the shaft, the moment of inertia of the rotor and shaft and the characteristic properties of the spring are selected so that the natural mechanical resonant frequency of the rotor and shaft is close to the frequency of the power supply.

U.S. Pat. No. 3,535,726 to Sawyer describes an electric toothbrush having an elongated handle containing an electric motor and a shaft attached to the electric motor. The shaft extends from an end of the handle and terminates in a brush head. The motor works to actuate the brush head in a variety of sinusoidal motions. The shaft external to the handle acts as a cantilever resonating beam and has the same resonant frequency as the power supply. The shaft is attached to the motor such that the rotation of the motor excites the shaft in an eccentric manner, thus creating the sinusoidal movement of the brush head. The movement of the brush head generates sonic waves to clean the teeth of the user.

U.S. Pat. No. 3,538,359 to Barowski describes an electric toothbrush having a handle containing an electric motor and a shaft attached to the motor and extending from the handle. The shaft terminates in a brush head. Upon actuation by the electric motor, the shaft oscillates about its longitudinal axis. Springs are attached to the armature to urge the armature to a rest position, and also facilitate the oscillating motion of the brush head. No mention is made of using resonating frequencies in the Barowski patent.

U.S. Pat. No. 4,787,847 to Martin, et. al., describes an electric toothbrush having an elongated handle from which extends a piezoelectric transducer having a brush head attached to its distal end. The piezoelectric transducer shaft is excited by an AC signal generated by a circuit within the handle. The circuit supplies a specific frequency signal to the shaft. The specific frequency is calculated to produce the desired resonant frequency vibration of the shaft. The resonant frequency of the transducer shaft is determined by its geometry.

U.S. Pat. Nos. 5,189,751 and 5,263,218 to Giuliani, describe an electric toothbrush having a toothbrush shaft driven by an electromagnetic motor. The toothbrush shaft, upon actuation by the motor, pivots about a pivot point to vibrate in a planar motion (up and down or side to side). A spring is utilized near the pivot point to urge the shaft toward its neutral position. The '218 patent has similar specification and claims as the '751 patent, however, the '218 claims further include an energy recovery circuit for storing reactive energy to eliminate or reduce the energy lost during operation.

The brush head vibrates at a frequency decided by the particular mass and pivot arrangement. The brush head, brush shaft, and pivot member are selected to have a natural mode of resonance at a predetermined frequency. If vibration at a resonant frequency is desired, the operating frequency of the drive system is selected to be relatively close to the resonant frequency of the mechanical system (brush head, brush shaft, pivot member). The drive system can be de-tuned to vibrate at an off-resonant frequency from the mechanical system. Upon a certain load being placed on the mechanical system, the frequency of vibration becomes resonant. Further loading then moves the vibration out of resonance. The characteristics of the brush head movement changes with loading.

The aforementioned patents do not describe a system by which the brush head vibration is maintained at resonance throughout use to obtain the benefits of resonant vibration for cleaning teeth. The driving signals and spring-mass systems for each design are carefully selected to obtain resonant frequency at a given load. There remains a need for an electric toothbrush that maintains the vibration of the brush head at its resonant frequency under the variety of loads encountered during use.

OBJECTS AND SUMMARY OF THE INVENTION

The principal object of the present invention is to provide an improved electric toothbrush.

Another object of the present invention is to provide an electric toothbrush having improved scrubbing performance.

A further object of the present invention is to provide an improved electric toothbrush that maintains the optimum scrubbing operation throughout the variety of loads encountered when in use.

In accordance with the foregoing objects, the present invention is embodied in an oscillating tool having particular but not necessarily exclusive utility as an electric toothbrush. The tool comprises a tubular handle housing defining an interior chamber and having an axial opening at one end. An electromagnetic motor is mounted in the chamber, the motor having an oscillatable armature. The armature is integrally formed with a mechanical oscillator, the mechanical oscillator having a resonant frequency. One end of the mechanical oscillator extends outwardly through the opening while the other end is attached to the housing inside the chamber.

A power source supplies an alternating current drive signal to the motor causing the armature and the mechanical oscillator to oscillate. An oscillation sensor is connected to the housing in the chamber and is in juxtaposition with the armature. The sensor generates a sensor signal in response to the oscillation of the armature and sends the sensor signal to a control circuit. The control circuit alters the frequency of the drive signal applied to the motor in response to the phase offset of the sensor signal.

The drive signal has a frequency substantially equal to the resonant frequency of the mechanical oscillator, causing the mechanical oscillator to oscillate at its resonant frequency. The sensor signal is an alternating current having a frequency, and the drive signal frequency and the sensor signal frequency have a fixed phase difference when the mechanical oscillator is oscillating at resonant frequency. The control circuit alters the drive signal to maintain the fixed phase difference under the variety of loads placed upon the mechanical oscillator while in use.

More specifically, the present invention comprises a new and improved oscillating tool/electric toothbrush where the mechanical oscillator comprises a drive shaft and a spring. The spring is operably attached to the lower end of the drive shaft and to the handle housing inside the chamber. A brush head assembly attaches to an upper end of the toothbrush, and is driven in oscillatory motion by the resonant motion of the mechanical oscillator when the motor is activated.

Other aspects, features and details of the present invention can be more completely understood by reference to the following detailed description of a preferred embodiment, taken in conjunction with the drawings, and from the appended claims.

BRIEF DESCRIPTION OF THE DRAWINGS

FIG. 6 is an enlarged view of the electric toothbrush with exterior portions cut away to expose an interior chamber.

FIG. 7 is a perspective view of the electric toothbrush inserted into a charging base.

DETAILED DESCRIPTION

Figure 1:
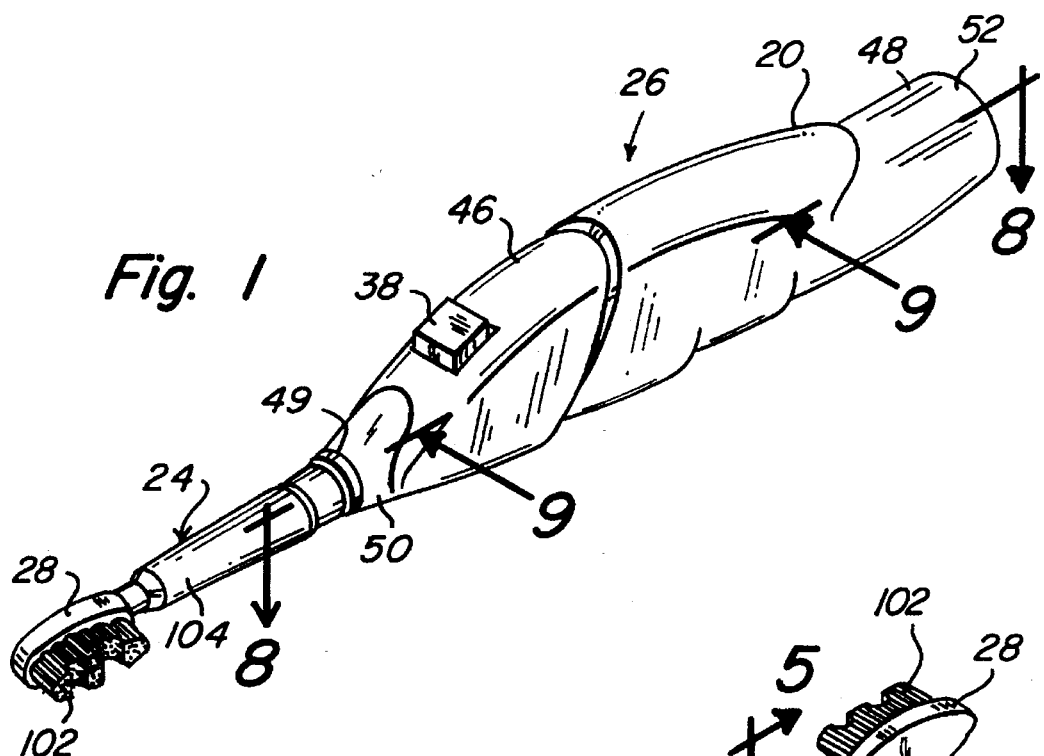
FIG. 1 is a perspective view of an electric toothbrush embodying the present invention.
Figure 2:
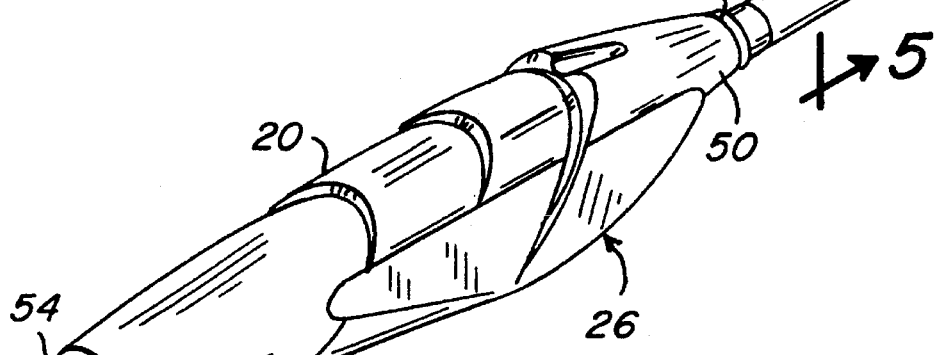
FIG. 2 is a perspective view from the opposite side of the electric toothbrush as shown in FIG. 1.
Figure 3:
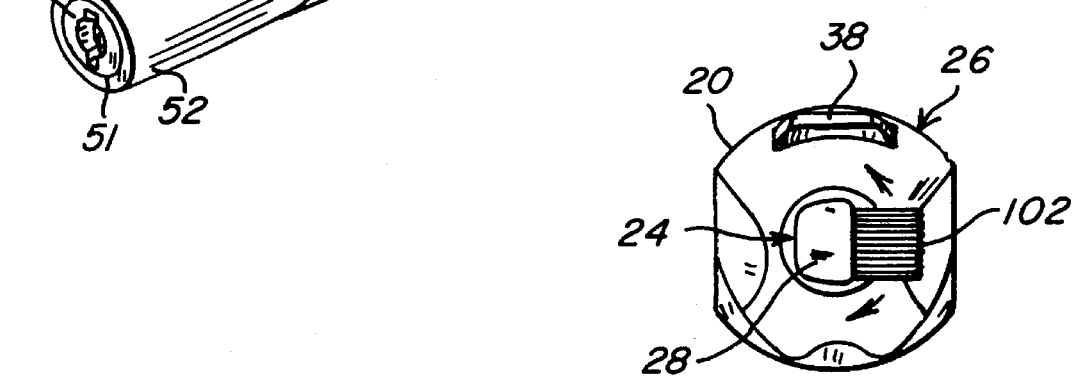
FIG. 3 is an end elevational view of the electric toothbrush as shown in FIG. 1.
Figure 4A:
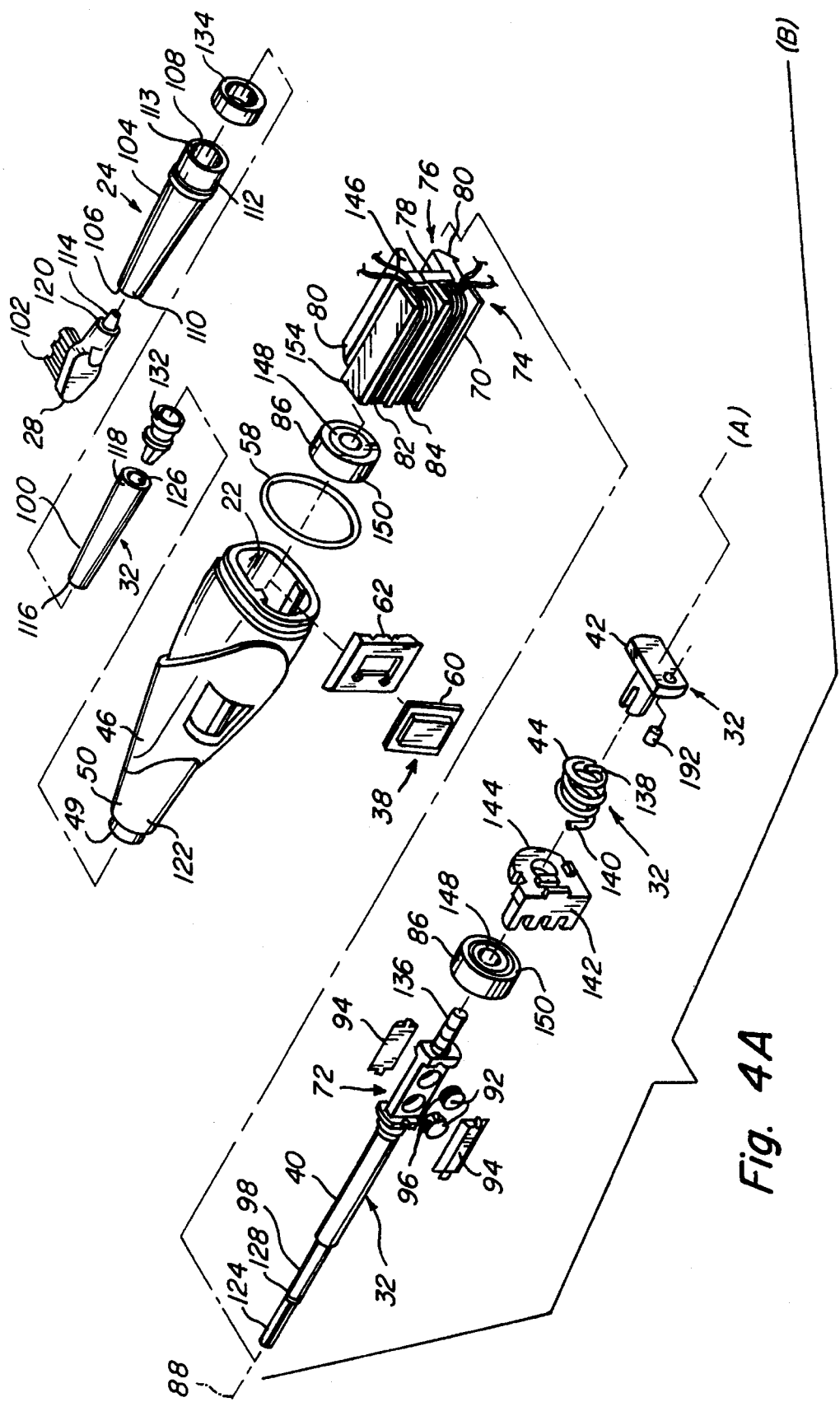
FIGS. 4a and b are an exploded view of the components of the electric toothbrush shown in FIG. 1.
Figure 5:
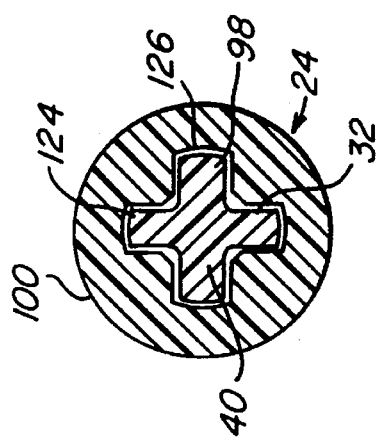
FIG. 5 is a section view taken substantially along the plane of line 5—5 of FIG. 2.
Figure 4B:
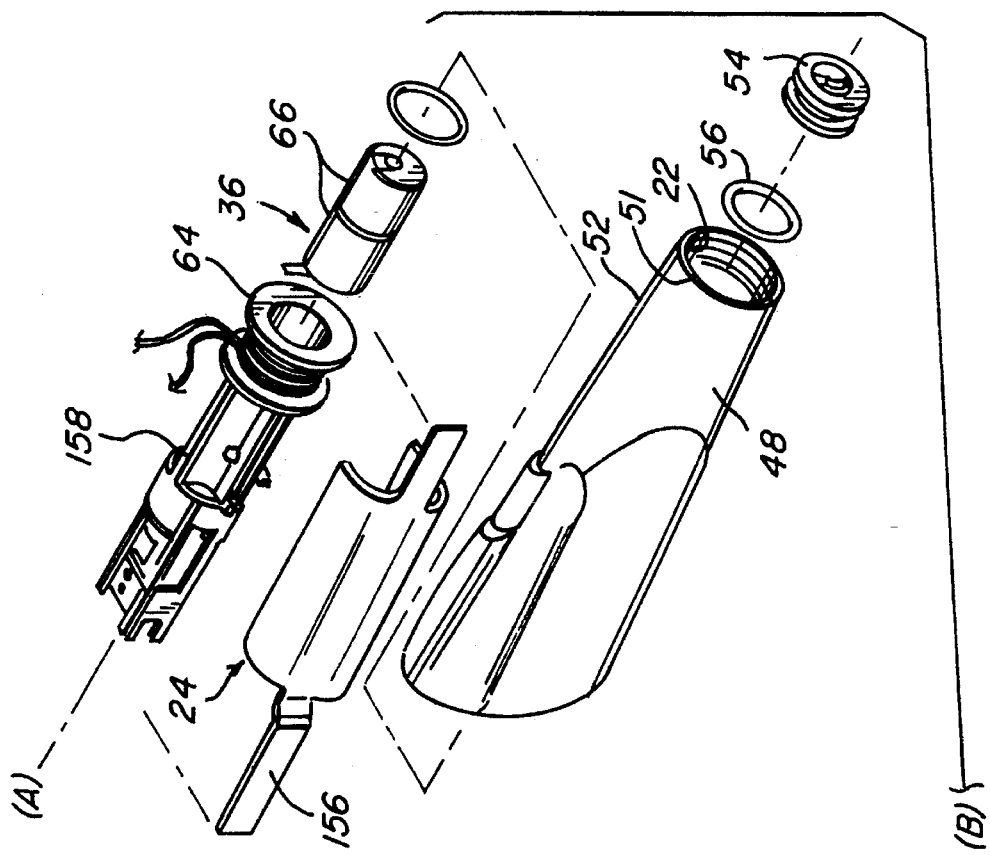

The present invention is embodied in an improved electric toothbrush 26 comprising an elongated tubular handle housing 20 defining an interior chamber 22, and an end effector or brush head assembly 24 extending from one end of the handle housing, as shown in FIGS. 1, 2, and 3. A motor 30, mechanical oscillator 32, control circuit 34, and power source 36, as shown in FIGS. 4, 5, 6, 8 and 9, are located within the interior chamber of the handle housing. The motor 30, mechanical oscillator 32, and control circuit 34 of the electric toothbrush 26 are operatively connected to achieve high-frequency operation in mechanical resonance to drive the brush head 28.

When in use, the user grips the electric toothbrush 26 around the handle housing 20 and activates the brush head assembly 24 by pressing an on/off switch 38 located on the handle housing. Activation of the on/off switch causes the brush head 28 to oscillate in a rotary manner about the longitudinal axis of the brush head assembly 24 at the resonant frequency of the mechanical oscillator 32 (FIGS. 4, 5, 6, 8 and 9), as indicated by the arrows in FIG. 3. Resonance is a vibration of large amplitude in a mechanical system caused by a relatively small periodic stimulus of the same or nearly the same period as the natural vibration period of the mechanical system.

The mechanical oscillator 32 which drives the brush head 28 comprises a drive shaft 40, a portion of the motor 30, a portion of the brush head assembly 24, as further described below, and a spring 44 connected to the drive shaft by a spring retainer 42. The mechanical oscillator has a resonant frequency dependent on the inertial mass of its parts and the stiffness of the spring. Resonant frequency oscillation allows for large amplitude, power efficient high frequency motion. The high frequency oscillation of the brush head 28, when engaging the user's teeth, acts to effectively and efficiently remove plaque and stains from the surface of the teeth, and also massages the gums.

FIGS. 4, 5, 6, 8 and 9 illustrate the handle housing 20 and the placement and inter-relation between the motor 30, drive shaft mechanical oscillator 32, control circuit 34 and power source 36. The handle housing comprises an upper half 46 and a lower half 48, together defining the interior chamber 22. The handle housing defines an aperture 49 at an upper end 50 and an aperture 51 at a lower end 52 for use in accessing the interior chamber. The aperture 51 has a removable plug 54 which is water tightly sealed, using an O-ring 56, in the aperture 51 when closed. The plug is removed to discard the power source 36 when necessary. The upper and lower halves 46, 48 of the handle housing 26 snap-fit together on an O-ring 58 forming a watertight seal.

The on/off switch activator 38 is a waterproof depression switch. The on/off switch activator turns the electric toothbrush 26 "on" by a first depression, and turns the electric toothbrush "off" by a second depression. The switch activator comprises a waterproof switch button 60 supported by a switch frame structure 62.

For supplying power to the electric toothbrush 26, a rechargeable power source is housed in the lower end of the handle housing 20. An inductive charging coil 64 recharges the power source when the lower end 52 of the handle housing is placed in a charging base 68, as shown in FIG. 7. The power source comprises a DC battery, preferably a pair of rechargeable DC batteries 66 connected in series. The charging base has a cord 69 and plug 71 to receive energy from a standard wall electrical outlet (not shown). The charging base has a recessed area 73 for holding the brush head assembly 24 when not in use.

The motor 30 comprises a stator 70 and an armature 72. The stator is fixed in location with respect to the handle housing 20 and comprises an electromagnet 74 with a ferromagnetic core. The stator has an elongated U-shape 76, with the ferromagnetic core as the base 78 of the U-shape. Each leg 80 of the elongated U-shape represents a magnetic pole, with the poles laterally opposing one another. The electromagnet of the stator comprises a pair of coils 82, 84 wound on a common axis around the ferromagnetic core. The commutation of the motor 30 is preferably controlled electrically, however mechanical commutation is contemplated.

Figure 10:
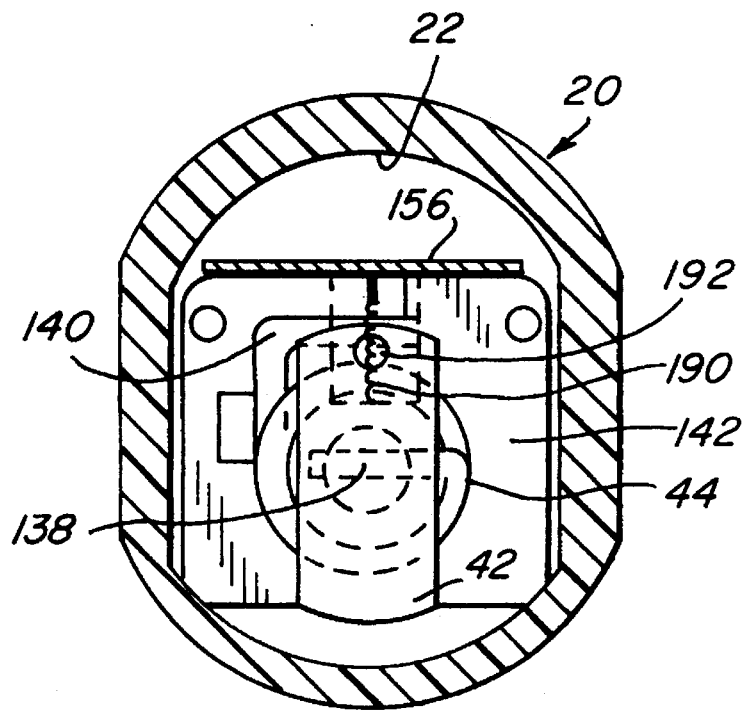
FIG. 10 is a section view taken substantially along the plane of line 10—10 of FIG. 9.

The armature 72 is an elongated shaft located between the laterally opposing legs 80 or poles of the stator 70, as shown in FIG. 10, and is rotatably supported in that location by a pair of bearings 86. The bearings 86 journal the armature for rotation relative to the stator, about a longitudinal axis 88. The armature thus acts as drive shaft 40. The armature comprises a permanent magnet 92 with magnetically conductive extensions 94. Preferably two circular permanent magnets 96 are placed side by side in the armature 72 with similarly oriented magnetic poles. The motor 30 is located generally at the center of the length of the handle housing 20.

The brush head assembly 24 consists of a brush head 28 rigidly attached to an upper end 98 of a subtantially frustoconical brush shaft 100. The brush head 28 has a plurality of bristles 102 extending outwardly therefrom to engage the user's teeth upon use of the electric toothbrush 26. A brush shaft housing 104, generally having an elongated tubular shape and defining an aperture 106, 108 at an upper end 110 and at a lower end 112, and also defining an elongated internal cavity 113, fits loosely over the brush shaft 100. The brush head 28 has a downwardly depending longitudinal extension 114 that inserts through the aperture 106 at the upper end 110 of the brush shaft housing 104 and into a cavity 116 at the upper end 98 of the brush shaft 100. The extension 114 is rigidly attached to the brush shaft 100. A shoulder 120 proximate to the extension 114 abuts the upper end 110 of the brush shaft housing 104. The brush head 28 and brush shaft 100, in this configuration, are able to rotate in conjunction freely with respect to the brush shaft housing 104.

To allow the brush head assembly 34 to be replaced, the brush head assembly is releasably operably attached to an upper end 122 of the handle housing. An upper end 124 of the drive shaft 40 is splined, and extends through the aperture 49 in the upper end 50 of the handle housing 20. The splined upper end 124 of the drive shaft 40 releasably inserts into and mates with a splined cavity 126 at a lower end 118 of the brush shaft 100. The splined fit between the drive shaft 40 and brush shaft 100 creates a tight coupling fit allowing the efficient transmission of torsional forces while minimizing any losses in amplitude of motion. The drive shaft 40 has an annular raised area 128 proximate to the upper splined end 124 that fits into an annular depression 130 on the interior of the splined cavity 126, providing a releasable snap-fit between the brush shaft 100 and the drive shaft 40.

For providing a watertight seal to keep moisture and other foreign matter from entering the interior chamber 22 of the handle housing, a flexible boot 132 fits over the drive shaft 40 and engages the handle housing 20 at the point where the drive shaft exits the upper end 50 of the handle housing. A collar 134 made of elastomeric material is attached to the lower aperture 108 of the brush shaft housing 104. The collar 134 not only acts to identify the brush head assembly 24 by color, but also acts to isolate the oscillating motion of the mechanical oscillator in the brush head 28.

Figure 8A:
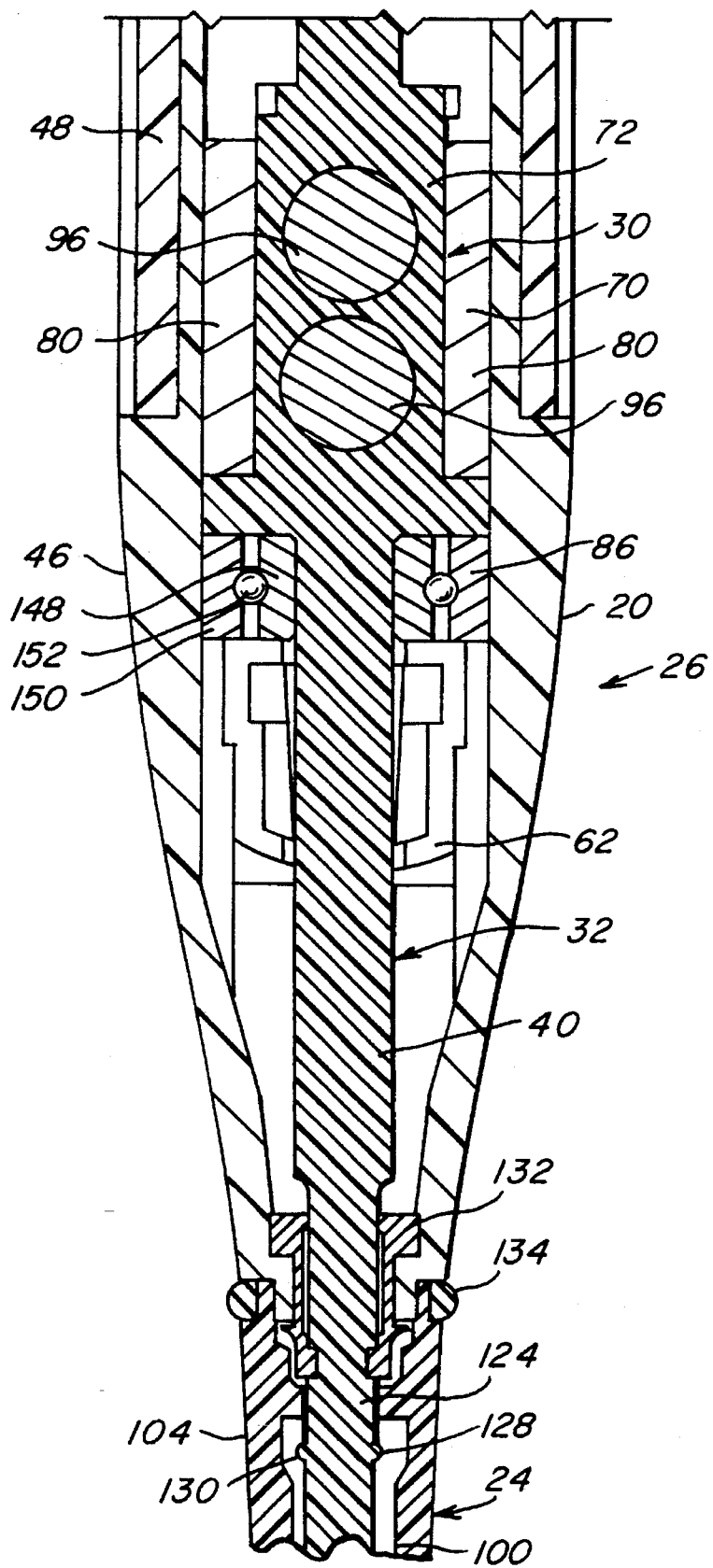
FIGS. 8a and b are a section view taken substantially along the plane of line 8—8 of FIG. 1.
Figure 8B:
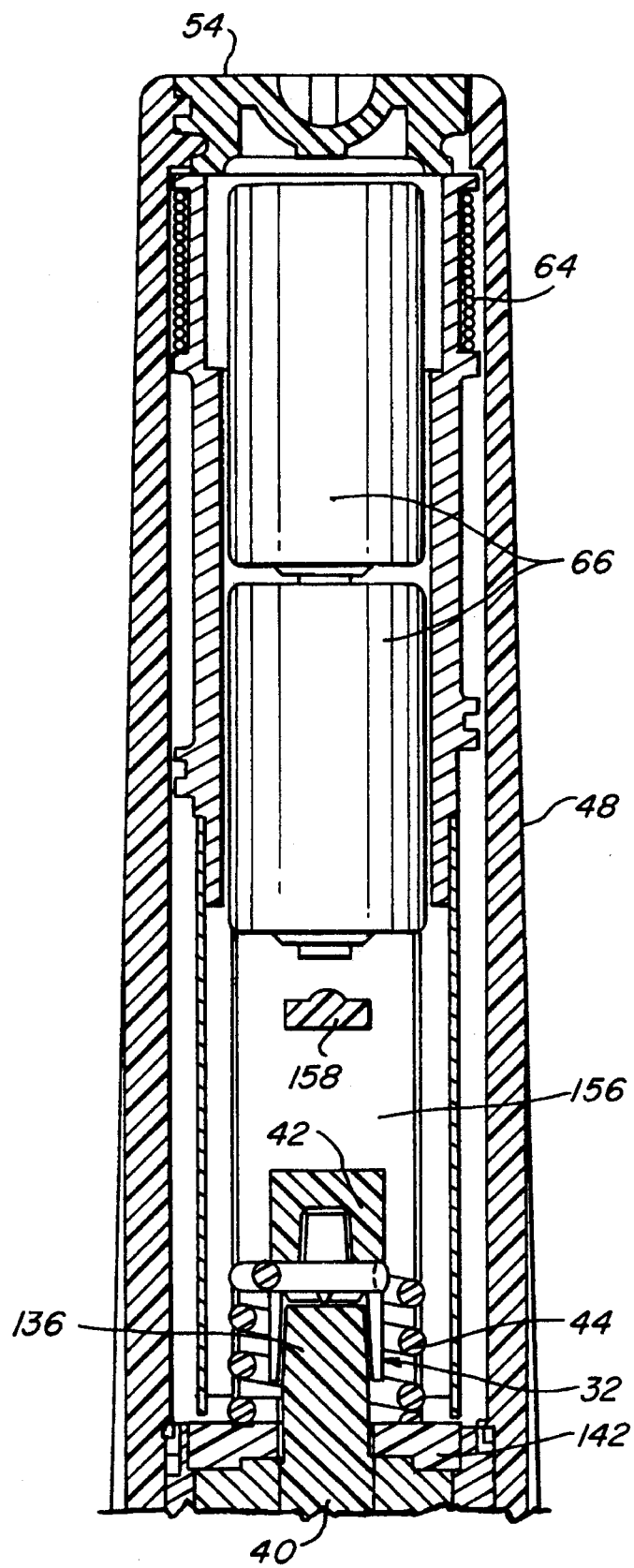
Figure 9:
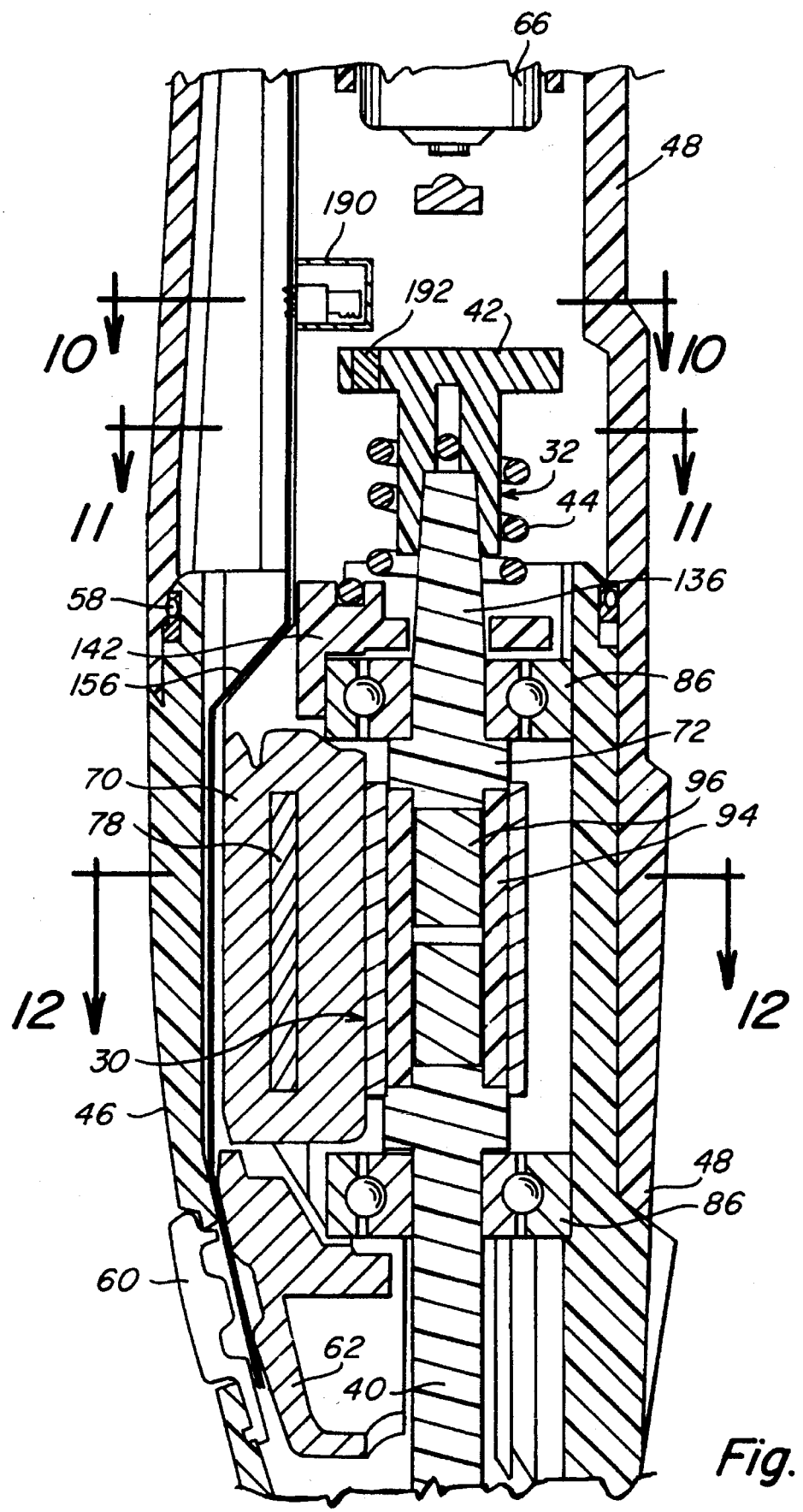
FIG. 9 is an enlarged partial section view taken substantially along the plane of line 9—9 of FIG. 1.

The mechanical oscillator 32 comprises a mass, a spring 44, and an excitor, such as the electromagnetic motor 30, to drive the oscillator in resonant motion. The mass of the mechanical oscillator 32 of the present invention is made up of the drive shaft 40, including the armature 72 near a lower end 136, the brush shaft 100, brush head 28, spring retainer 42 and a portion of the spring 44. The spring 44 is a coil spring in the preferred embodiment, and operates in torsion around the longitudinal axis of the coil. As shown in FIGS. 8 and 9, the coil spring is attached to the lower end 136 of the drive shaft 40 by the spring retainer 42. A lower end 138 of the spring is attached to the spring retainer, and the spring retainer is attached to the drive shaft 40 so that the longitudinal axis of the drive shaft is substantially the same as the longitudinal axis of the coil spring. The lower end 136 of the drive shaft 40 fits within the inner diameter of the coil spring 44 in order to conserve space. The integral relationship of the armature 72 within the structure of the mechanical oscillator 32 is a unique feature of this motor construction.

One end 140 of the coil spring 44 is fixed in place within the chamber 22 of the handle housing 20, preferably by a stator cap 142. The stator cap is located between the armature 72 portion of the drive shaft 40 and the lower end 136 of the drive shaft. The stator cap has an axial hole 144 through which the drive shaft extends. The stator cap is fixed in position within the interior chamber of the handle housing, and partially abuts a lower end 146 of the stator.

The stiffness characteristics of the parts that make up the inertial mass of the mechanical oscillator, including the brush head 28, brush shaft 100, drive shaft 40, and spring retainer 42 results in the spring rate and torsional properties of the mechanical oscillator being substantially due only to the coil spring 44. The natural resonant frequencies of the variety of parts that comprise the mass portion of the mechanical oscillator are designed to be very different (higher) from the resonant frequency of the mechanical oscillator. This difference helps maximize the efficiency of transmission of the oscillation motion through the drive shaft and associated parts.

The drive shaft 40 is preferably maintained in radial position along the longitudinal axis of rotation of the armature 72 by roller bearings 86, each having an inner race 148, an outer race 150, and ball bearings 152. One roller bearing is at the upper end 124 of the drive shaft 40, while the other is at the lower end 136 of the drive shaft. The upper roller bearing supports the drive shaft proximate to an upper end 154 of the stator 70. A lower bearing supports the drive shaft between the armature 72 and the lower end 136 of the drive shaft. The outer races 150 of both of the bearings are fixed in position within the interior chamber of the handle housing. The inner races 148 of each of the bearings are operably attached to the drive shaft to allow the drive shaft to rotate while prohibiting any substantial side-to-side movement. It is contemplated that other types of bearings having adequate frictional qualities could be used.

The stiffness characteristics of the coil spring 44 in the preferred embodiment provides sufficient thrust bearing capacity to handle the thrust load placed on the drive shaft 40 through the brush head 28 during use.

While the preferred embodiment for the spring-mass system for the mechanical oscillator 32 is preferably the coil spring 44 attached to the drive shaft 40, other "spring-mass" embodiments are possible. For example, a torsion bar, which combines the mass and spring in one body may be utilized. Also, an elastomeric mass encapsulating the drive shaft to act as a spring, or a flat spring mounted perpendicular to the axis of rotation to supply the desired spring rate by acting as a beam in bending under the applied moment couple may be used. Further, multiple-frequency oscillators may also be designed to be controlled to maintain a multiple of resonant frequency motion, or combinations thereof, under a variety of loads.

A flexible integrated circuit board 156 containing the circuitry for operating the electric toothbrush 26 of the present invention is bent around the internal circumference of the interior chamber 22 of the handle housing 20. An internal framework bobbin carrier 158 supports the integrated circuit board while also holding the power source 36 and induction charging coil 64. The bobbin carrier 158 is fixed in position inside the interior chamber 22 of the handle housing.

Figure 14:
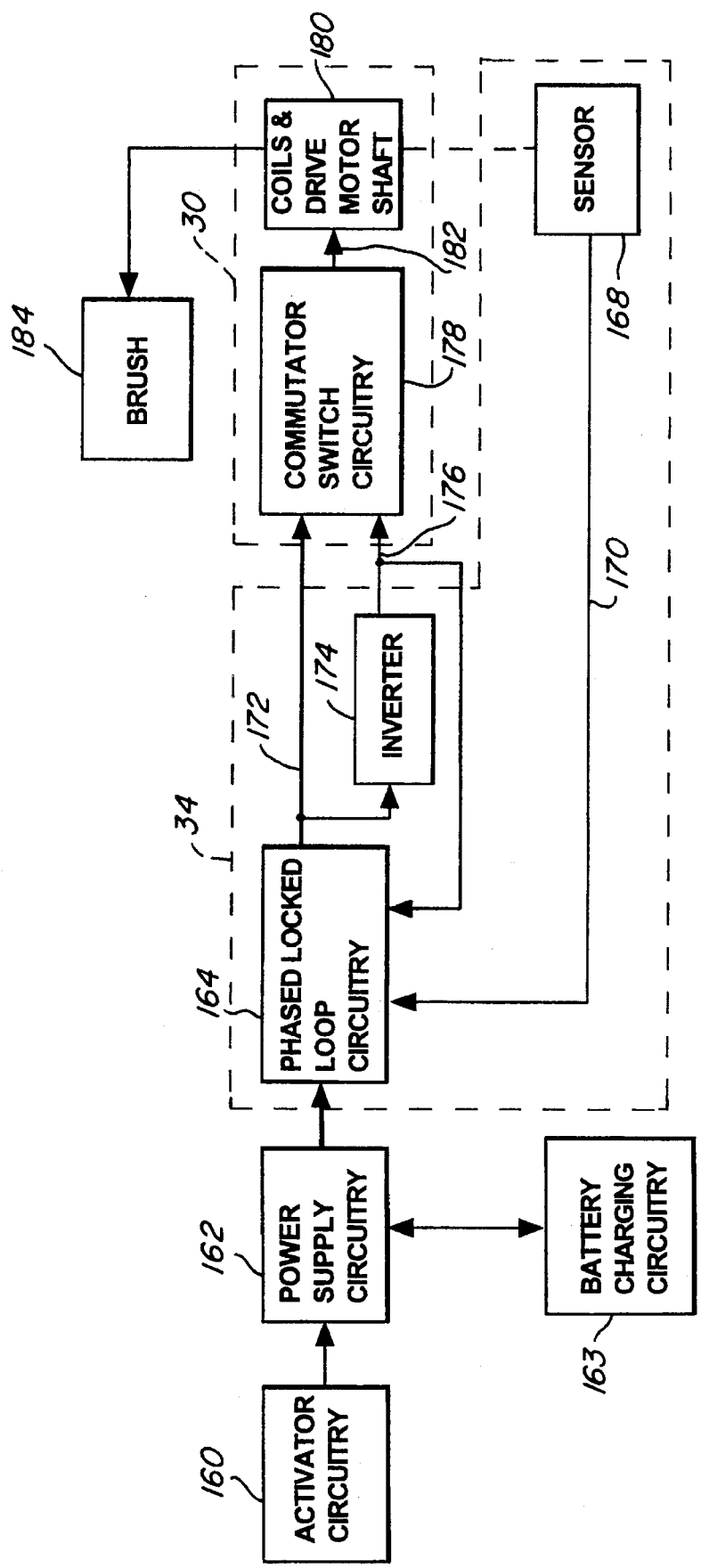
FIG. 14 is a block diagram of the circuitry involved in the operation of the present invention.

FIG. 14 illustrates the electrical design for operating the electric toothbrush 26. The majority of the electrical design relates to the commutation of the motor 30 in a manner which operates the mechanical oscillator 32 at its resonant frequency of vibration.

Activator circuitry 160 includes the on/off switch 38, described previously, which is activated by a user of the electric toothbrush 26 alternately to power and to turn off the toothbrush 26. When the user of the toothbrush 26 activates the on/off switch 38 of the activator circuitry 160, the power supply circuitry 162 which includes the DC batteries 66 and the power source 36 causes energy stored by the DC batteries 66 to be applied to the control circuit 34 and, in turn, to the motor 30. Battery charging circuitry 163 is coupled to the power supply circuitry 162.

The control circuit 34 includes phase-locked loop circuitry 164 which is powered by the operation of the power supply circuitry 162 by way of the line 166 and is coupled to receive signals by a sensor 168 on line 170. The phase-locked loop circuitry 164 is operative to generate control signals on line 172. Line 172 is coupled directly to the motor 30 and to an inverter circuit 174. The inverter circuit 174 inverts the values of the control signals generated on line 172 and generates inverted signals on line 176 which are also applied to the motor 30. Line 176 is also coupled to an input of the phase-locked loop circuitry 164.

More particularly, the control signals generated on line 172 and the inverted signals generated on line 176 are applied to commutator switch circuitry 178 of the motor 30. The commutator switch circuitry 178 includes commutating switches, preferably transistor switches, which, when in selected switch positions, selectively provide operative power to the coils 82, 84 of the coils and drive motor shaft 180 by way of lines 182. The drive shaft 40 of the coils and drive motor shaft 180 oscillates, in manners described previously, to effectuate motion of the brush 184 which comprises the brush head 28 and the brush shaft 100, described previously.

Oscillation of the drive shaft of the coils and drive motor shaft 180 is sensed by the sensor 168 and signals of values representative of the position of the drive shaft are generated on line 170 to be provided to the phase-locked loop circuitry 164. The control signals generated by the phase-locked loop circuitry 164 control the switch positions of the switches of the commutator switch circuitry 178 in manners to control the relative phase between the frequency at which power is applied to the coils 82, 84 and the oscillation frequency of the drive shaft. By appropriate activation and deactivation of the switches of the commutator switch circuitry 178, the desired phase difference may be maintained.

The sensor 168 generates the signal on line 170 which is coupled to the phase-locked loop circuit 164 to permit the resonant oscillation of the mechanical oscillator 32 to be maintained under a variety of loads. The phase difference oscillation of the drive shaft 40 and that of the power applied to the stator electromagnetic coils 82, 84 is a known value at resonance, and shifts away from that point in a predictable fashion. The control signals generated by the circuit 164 cause operation of the commutator switch circuitry 178 at a frequency determined to maintain the phase difference necessary for resonant frequency oscillation regardless of the load while in use.

Figure 11:
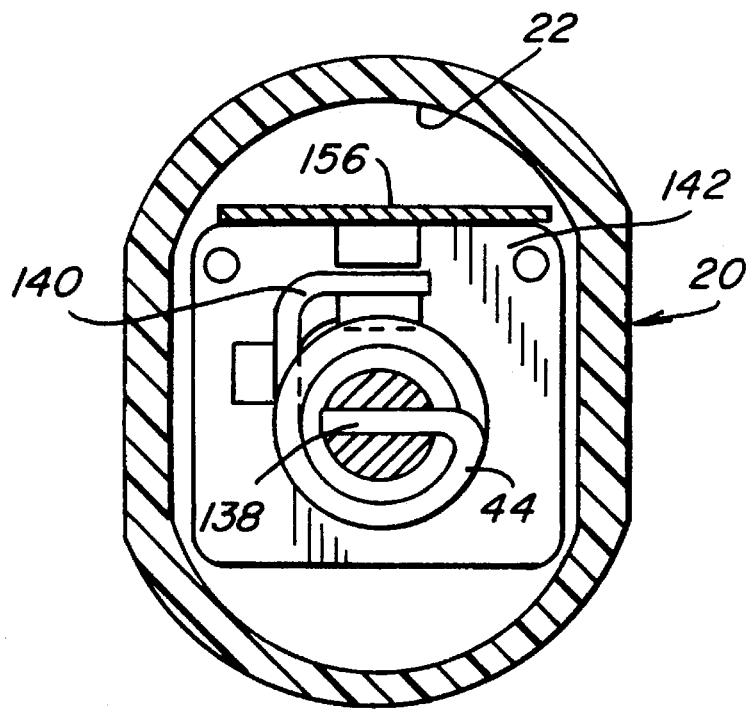
FIG. 11 is a section view taken substantially along the plane of line 11—11 of FIG. 9.
Figure 12:
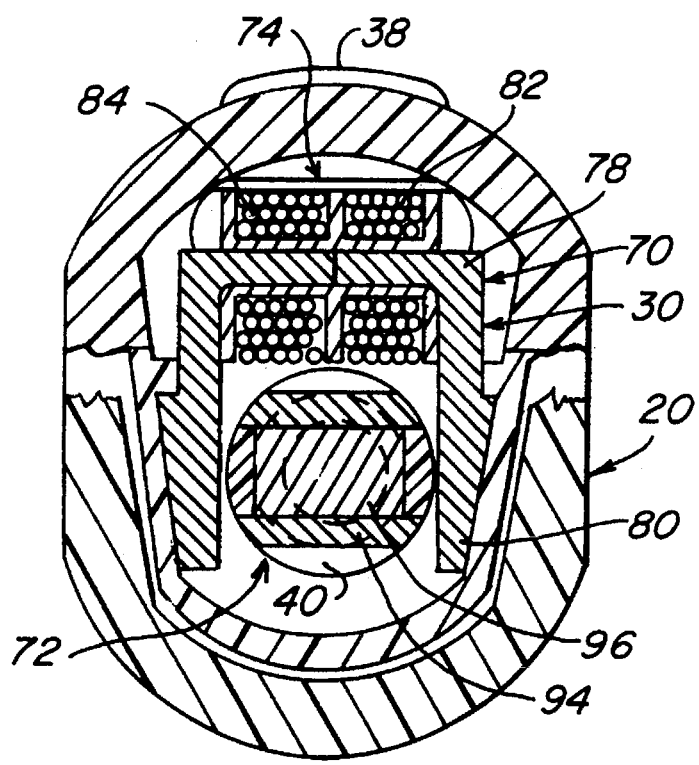
FIG. 12 is a section view taken substantially along the plane of line 12—12 of FIG. 9.
Figure 13:
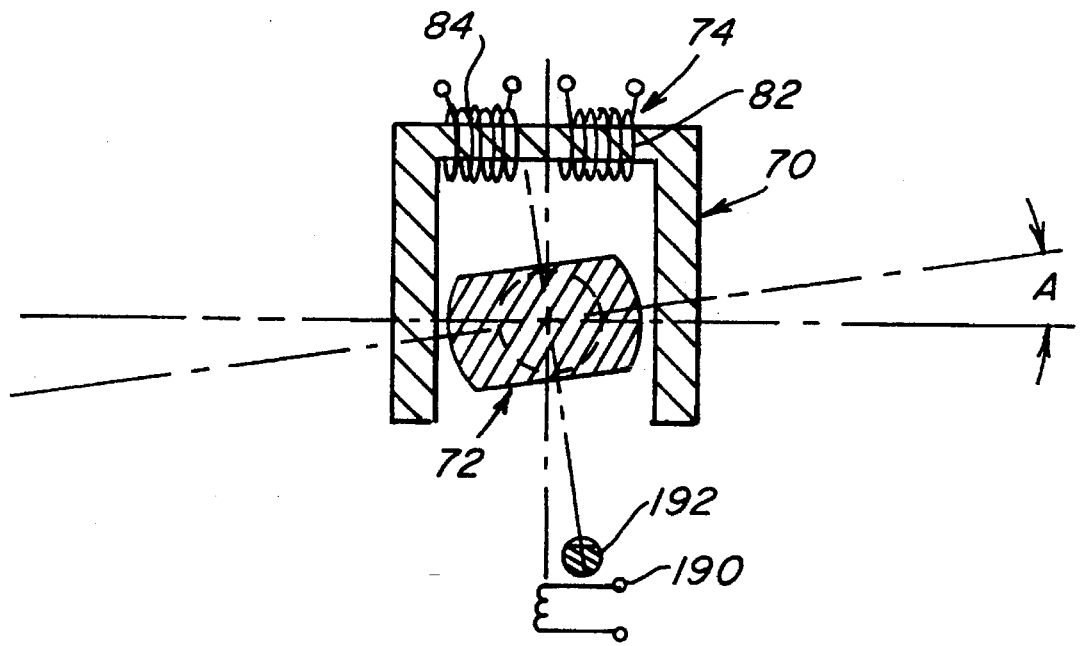
FIG. 13 is a schematic diagram of the electromagnetic motor components and feedback sensor during rotation.

Preferably the sensor 168 is a magnetic sensor comprising a sensor coil 190 and a sensor permanent magnet 192, as shown in FIGS. 7 and 11. The sensor permanent magnet is mounted on the spring retainer 42, and the sensor coil 190 is located on the circuit board 156 proximate to the location of the sensor magnet 192. The motion of the drive shaft 40 when the motor 30 is excited causes the sensor magnet 192 to move past the sensor coil 190 at the frequency of oscillation of the drive shaft, thus generating the signal on the line 170 representative of the frequency of oscillation of the drive shaft 40. The line 170 is provided to the circuitry 164 so the circuitry 164 can continually control the commutator switch activation of the commutator switch circuitry 178 as necessary.

A magnetic sensor is preferred because the magnetic sensor acts as a differentiator and thus the sensor signal is proportional to velocity. Velocity feedback is relatively insensitive to placement of the sensor itself, permitting greater tolerance on where the sensor is located during manufacturing. Polarity of sensor placement relative to the driving signal at the stator is important to minimize the effect of the magnetic field of the stator on the sensor coil 190.

There is a capture range of frequencies in which the frequency of signal generated on line 170 must be located in order for the circuitry 164 to operate correctly. The capture range is determined by the design of the phase-locked loop circuitry 164 and by the ability of the sensor 168 to sense adequately the motion of the sensor magnet 192 and provide the signal on line 170. The resonant frequency of the mechanical oscillator 32 must be within the capture range in order for the circuitry 164 to maintain the mechanical oscillator in resonant frequency oscillation. If the initial driving of the coils 82, 84 is within this capture range, oscillation of the armature 72 is caused at an adequate frequency for the circuit to lock onto the correct phase difference and oscillate the mechanical oscillator 32 at resonant frequency. The capture range of the present invention is about 200 Hz to about 300 Hz. The phase-locked loop circuitry also has a lock range in which it will continue to maintain the desired phase relationship, the lock range being different from the capture range.

When the toothbrush 26 is activated, the power source 36 of the power supply circuitry 162 powers the motor 30 by way of the control circuit 34 to cause potentials to be applied to the electromagnetic coils 82, 84 on the stator 70. The potential to the coils 82, 84 generates a magnetic field with a pole in each of the legs 80 of the U-shaped stator. The electromagnetic field makes the armature 72 experience a moment couple which causes the armature to rotate in a manner to attempt to align its poles with those of the electromagnet. As the armature rotates, its movement is resisted by the coil spring 44. When the drive signal provides potential to force the armature in the opposite direction, the armature again will be resisted by the coil spring. When the potential is removed from the electromagnetic coil, regardless of the direction of the rotation of the armature, the coil spring provides a restoring force to the armature. The amplitude of rotation for the preferred embodiment of the present invention is up to about 14° off of center, as denoted by A in FIG. 11. It is contemplated that the amplitude of motion can be modified for almost any desired range by modifying the geometry of the motor 30 and the spring-mass characteristics of the mechanical oscillator 32.

The oscillation of the armature 72 causes the entire drive shaft 40 to move accordingly within the bearings 86. The drive shaft is operably connected to the brush shaft 100 by a spline joint, as previously described. The spline joint is an efficient coupling and minimizes any motion losses through the connection. The rigid connection between the brush shaft and brush head 28 also minimizes any motion losses. The brush head and brush shaft are able to move freely within the brush shaft housing 104 without any substantial adverse affect (such as damping or loading) on the resonant oscillation from the brush shaft housing. The collar 134 provides vibration isolation to the brush shaft housing 104 and helps concentrate the oscillation of the mechanical oscillator 32 in the brush head 28.

The oscillation of the mechanical oscillator 32, or the drive shaft 40 specifically, is sensed by the sensor 168, and signals indicative of the oscillation are generated on line 170. The circuitry 164 generates control signals on line 172, and, in turn, inverted signals are generated upon line 176 to adjust the rate at which the switches of the commutator switch circuitry 178 are opened and closed, thus to drive the mechanical oscillator 32 at resonant frequency.

When a load is placed on the mechanical oscillator 32, such as when electric toothbrush 26 is used to brush one's teeth, the frequency of oscillation is affected. The sensor 168 generates signals on line 170 representative of the new frequency of the drive shaft 40 due to the load, which causes the circuitry 164 to produce control signals on line 172, to maintain the known phase difference in order to keep the mechanical oscillator oscillating at resonant frequency under the applied load. The circuitry 164 is thus capable of maintaining resonant frequency oscillation of the mechanical oscillator 32 under a variety of loads, provided that the resonant frequency of the mechanical oscillator, given a certain load, is within the lock range of the control circuit.

The continuous adjustment of the drive signal by the circuit 164 to maintain resonant frequency oscillation under a variety of loads has several benefits. The major benefit is the tooth-cleaning performance, which is always at a maximum amplitude of brush head movement, and hence at maximum brushing efficiency because the mechanical oscillator is always running at resonance. Another is the impact on manufacturing costs. Because the circuitry 164 is in effect self-adjusting within the capture range, the operation of the present invention is fairly insensitive to variations in the physical tolerances of the piece-parts used in manufacturing, thus reducing many manufacturing costs, including inspection and testing. The spring rate or inertial mass characteristics of the mechanical oscillator 32 may reasonably vary without affecting the performance of the present invention. Available electric toothbrushes operating at resonance are more costly to manufacture because their performance is extremely sensitive to variations in the characteristics of the mechanical oscillator.

The preferred embodiment discloses the use of the present invention for electric powered tooth brushing having a rotary oscillating motion. It should be understood that the present invention is contemplated to be suitable to provide resonant oscillation in any motion where small amplitude and high frequency motion under a light to moderate load is desired. This would include, but not be limited to, scrubbing, polishing, stirring, mixing, blending, agitating, or engraving.

A presently preferred embodiment of the present invention and many of its improvements have been described with a degree of particularity. This description has been made by way of a preferred example and is based on a present understanding of knowledge available regarding the invention. It should be understood, however, that the scope of the present invention is defined by the following claims, and not necessarily by the detailed description of the preferred embodiment.

I claim:

1. An oscillating tool comprising:
   a. a tubular handle housing defining an interior chamber and an axial opening at one end thereof,
   b. an electromagnetic motor mounted in said chamber, said motor including an oscillatable armature,
   c. a mechanical oscillator having a first end and a second end, said mechanical oscillator integrally formed with said armature, said mechanical oscillator having a resonant frequency, said first end of said mechanical oscillator extending outwardly beyond said housing through said opening, and said second end being operably attached to said handle housing,
   d. a power source operatively connected to said motor, said power source supplying an alternating current drive signal to said motor actuating said armature and said mechanical oscillator to effect oscillation thereof,
   e. an oscillation sensor mounted on said housing in juxtaposition with said armature and generating a sensor signal in response to the oscillation of said armature, and
   f. a control circuit receiving said sensor signal and altering the frequency of said drive signal applied to said motor in response to said sensor signal.

2. An oscillating tool as defined in claim 1, wherein said drive signal has a frequency substantially equal to the resonant frequency of said mechanical oscillator, causing said mechanical oscillator to oscillate at said resonant frequency.

3. An oscillating tool as defined in claim 2, wherein:
   a. said sensor signal is an alternating current based on the oscillation of said mechanical oscillator,
   b. the frequency of said drive signal and the frequency of sensor signal having a fixed phase difference therebetween when said mechanical oscillator is oscillating at said resonant frequency, and
   c. said control circuit altering said drive signal to maintain said fixed phase difference.

4. An oscillating tool as defined in claim 3, wherein said mechanical oscillator further comprises a drive shaft having an upper end and a lower end, and a spring, said spring operably attaching said lower end of said drive shaft to said interior chamber.

5. An oscillating tool as defined in claim 4, wherein said spring is a coil Spring defining a substantially tubular shape and having an upper end and a lower end, said lower end of said shaft being inserted into said coil spring and operably attached to said lower end of said spring, and said upper end of said spring being fixed within said interior chamber.

6. An oscillating tool as defined in claim 1, further comprising a brush head assembly being operably attached to said first end of said mechanical oscillator.

7. An oscillating tool as defined in claim 6, wherein said brush head assembly comprises an elongated brush shaft, a brush head rigidly attached to said brush shaft, said brush head having a plurality of bristles extending therefrom, and a hollow elongated brush shaft housing, said brush shaft inside said brush shaft housing, an upper end of said brush shaft housing journaling said brush head and brush shaft and allowing said brush shaft and brush head to rotate independently of said brush shaft housing, and wherein a lower end of said brush shaft engages said first end of said mechanical oscillator causing said brush shaft to oscillate concurrently with said mechanical oscillator.

8. An oscillating tool comprising:
   a. a handle housing defining an interior chamber;
   b. an electromagnetic motor having a oscillatable armature, said armature having a portion positioned in said interior chamber;
   c. a drive shaft integrally formed with said armature and extending longitudinally inside said interior chamber, and having an upper end extending through said housing;
   d. a spring having an upper end operably attached to said handle housing and a lower end attached to a lower end of said drive shaft, said drive shaft and spring in conjunction having a resonant frequency,
   e. a power source operatively connected to said motor, said power source supplying an alternating current drive signal to said motor for actuating said armature and said drive shaft and said spring to effect oscillation thereof,
   f. an oscillation sensor mounted in said housing in juxtaposition with said armature and generating a signal in response to the oscillation of said armature, and
   g. a control circuit receiving said sensor signal and altering the frequency of said drive signal applied to said motor in response to said sensor signal.

9. An oscillating tool as defined in claim 8, wherein said drive signal has a frequency substantially equal to the resonant frequency of said drive shaft and said spring, causing said drive shaft and said spring to oscillate at said resonant frequency.

10. An oscillating tool as defined in claim 9, wherein:
    a. said sensor signal is an alternating current based on the oscillation of said drive shaft and said spring
    b. the frequency of said drive signal and the frequency of said sensor signal having a fixed phase difference therebetween when said drive shaft and said spring are oscillating at said resonant frequency, and
    c. said control circuit altering said drive signal to maintain said fixed phase difference.

11. An oscillating tool as defined in claim 10, wherein said spring is a coil spring defining a substantially tubular shape and having an upper end and a lower end, said lower end of said shaft being inserted into said coil spring and operably attached to said lower end of said spring, and said upper end of said spring being fixed within said interior chamber.

12. An oscillating tool as defined in claim 8, further comprising a brush head assembly being operably attached to said upper end of said drive shaft.

13. An oscillating tool as defined in claim 12, wherein said brush head assembly comprises an elongated brush shaft, a brush head rigidly attached to said brush shaft, said brush head having a plurality of bristles extending therefrom, and a hollow elongated brush shaft housing, said brush shaft inside said brush shaft housing, an upper end of said brush shaft housing journaling said brush head and brush shaft and allowing said brush shaft and brush head to rotate independently of said brush shaft housing, and wherein a lower end of said brush shaft engages said upper end of said drive shaft causing said brush shaft to oscillate concurrently with said drive shaft.

14. A brush head assembly for an electric toothbrush having a splined drive shaft, said brush head assembly comprising:
   a brush shaft housing, an elongated brush shaft journalled in said brush shaft housing and having a first end and a second end, a brush head rigidly attached to said first end of said brush shaft and journalled on and extending from said housing, wherein said brush shaft is substantially frusto-conical in shape, and a plurality of bristles extending from said brush head, said second end of said brush shaft defining a splined cavity for releasably receiving said splined drive shaft.

15. A brush head assembly for an electric toothbrush having a splined drive shaft wherein said drive shaft defines an annular raised area, said brush head assembly comprising:
   a brush shaft housing, an elongated brush shaft journalled in said brush shaft housing and having a first end and a second end, a brush head rigidly attached to said first end of said brush shaft and journalled on and extending from said housing, and a plurality of bristles extending from said brush head, said second end of said brush shaft defining a splined cavity and an annular depression adjacent said splined cavity for releasably engaging said annular raised area on said drive shaft when said splined drive shaft is inserted in said cavity.

16. An oscillating tool comprising:
   a. a tubular handle housing defining an interior chamber and an axial opening at one end thereof;
   b. a mechanical oscillator having a resonant frequency and defining a first end and a second end, said first end of said mechanical oscillator extending outwardly beyond said housing through said opening, and said second end being operably attached to said handle housing;
   c. means for actuating said mechanical oscillator to effect oscillation thereof;
   d. means for sensing the movement of said mechanical oscillator;
   e. means for generating a sensor signal in response to the oscillation of said mechanical oscillator; and
   f. means for altering the oscillation of said mechanical oscillator in response to said sensor signal.

17. An oscillating tool as defined in claim 16, wherein said mechanical oscillator oscillates at said resonant frequency.

18. An oscillating tool as defined in claim 17, wherein:
   a. said sensor signal is an alternating current responsive to the oscillation of said mechanical oscillator;
   b. said means for actuating said mechanical oscillator further comprises an alternating current drive signal having a frequency, the frequency of said drive signal and the frequency of said sensor signal having a fixed phase difference therebetween when said mechanical oscillator is oscillating at said resonant frequency; and
   c. said means for altering the oscillation of said mechanical oscillator controls said drive signal to maintain said fixed phase difference.

* * * * *